United States Patent [19]

Singer et al.

[11] 4,270,383
[45] Jun. 2, 1981

[54] METHOD AND APPARATUS FOR MEASURING STRENGTH CHARACTERISTICS

[75] Inventors: Alfred R. E. Singer, Sketty; Russell W. Evans, Caswell, both of Wales

[73] Assignee: National Research Development Corporation, London, England

[21] Appl. No.: 93,498

[22] Filed: Nov. 13, 1979

[30] Foreign Application Priority Data

Nov. 15, 1978 [GB] United Kingdom ............ 44575/78

[51] Int. Cl.³ ............................................. G01N 3/48
[52] U.S. Cl. ........................................................ 73/82
[58] Field of Search ................. 73/81, 82, 85, 15.4, 73/15.6, 78

[56] References Cited

U.S. PATENT DOCUMENTS

| 2,323,925 | 7/1943 | Markwardt | 73/81 |
| 3,339,404 | 9/1967 | Brooks et al. | 73/82 |

FOREIGN PATENT DOCUMENTS

| 1096643 | 1/1961 | Fed. Rep. of Germany | 73/81 |
| 1132219 | 3/1957 | France | 73/81 |
| 616558 | 7/1978 | U.S.S.R. | 73/81 |

*Primary Examiner*—Donald O. Woodiel
*Attorney, Agent, or Firm*—Cushman, Darby & Cushman

[57] ABSTRACT

An apparatus and method for measuring the flow stress of metals and other material and like characteristics especially at hot working temperatures. The specimen is struck simultaneously by projectiles of equal mass but unequal velocity. The velocities of the projectiles and the dimensions of the different indentations produced upon the specimen by the projectiles are terms in the formula by which the flow stress is calculated. A formula requiring only two projectiles is adequate for many materials; one requiring three projectiles may be better for materials that show work-hardening when they undergo strain at high temperature. The projectiles may be propelled pneumatically or by contact with a driven lever. Alternatively the projectiles may be in the form of masses carried as pendulums.

14 Claims, 4 Drawing Figures

METHOD AND APPARATUS FOR MEASURING STRENGTH CHARACTERISTICS

METHOD AND APPARATUS FOR MEASURING STRENGTH CHARACTERISTICS

This invention relates to the measurement of strength characteristics such as flow stress. It relates especially to a method of such measurement that requires only compact apparatus, capable of being operated in a laboratory for example, and particularly to apparatus in which the specimen can easily be tested at those temperatures normally used in hot working, that is to say temperatures not less than half the absolute melting point or solidus temperature.

The range of known equipment capable of measuring flow stress and related characteristics of hot specimens includes hot tensile and torsion testing machines, hot hardness testers and plastometers. Known hot tensile and torsion testing machines can operate over a wide range of strain rates but they are expensive and require machined specimens and associated equipment. They also tend to have long cycle times. Hot hardness testers are widely used but have the double disadvantage of operating only at very low strain rates and of the complexity that they require inert operating atmospheres; like the machines already described they are also very expensive. Plastometers are of relatively recent origin and can give a useful range of operation, but the total cycle time of their operation tends to be long and the results of tests need careful interpretation in view of the complex effects that specimens undergo within such apparatus.

The principle behind the present invention is quite different from that of any of the types of machines just described, and opens up the possibility of relatively cheap apparatus in which small specimens, whose shape and size within reasonable limits is not critical, can be tested quickly in the hot working range. In particular the invention allows the specimen to be pre-heated in any convenient furnace with any required atmosphere control and transferred rapidly to the measurement apparatus, and for the critical steps in the method to be completed within a few seconds. This avoids the complexities of temperature maintenance required with many existing methods due to the extended time that they take.

The invention includes apparatus to measure strength characteristics of a specimen and comprising means to support the specimen, to launch at least two projectiles so that they strike it in free flight and at different speeds but substantially simultaneously and to ascertain those speeds, whereby the characteristic may then be determined by calculations including those speeds and the dimensions of the indentations made upon the specimen by the projectiles. The speed ascertaining means may comprise pairs of optical sensors, mounted at locations spaced from each other but each close to the free-flight trajectory of a projectile, and means to illuminate the two sensors by beams that the projectile intercepts in succession in flight. As one alternative the speed-ascertaining means may comprise pairs of spaced sensor coils located close to the specimen with electrical means to detect the successive passages of a projectile through each coil of the pair. With such speed-ascertaining means, the speed of a projectile may be calculated from the distance between the sensors and the time of transit of the projectile between them. Alternatively the speed might be dictated and ascertained simply by the geometry of the system by which the projectiles are launched and guided towards the specimen.

The projectiles may be in the form of masses carried in pendulum fashion by swinging arms, preferably so arranged that the centres of gravity of the masses are at the lowest point of their swing and thus travelling horizontally when they strike the specimen. If the arms are of equal length and pivoted on a common axis, impact of the masses with the specimen simultaneously but at different speeds may be achieved simply by releasing the arms simultaneously from starting positions in which they lie at different angles to the vertical.

Alternatively the projectiles may be fired upwardly at the underside of the specimen, and may travel within tubes for guidance and/or safety. Such projectiles may be fired pneumatically for instance, or by being driven by a lever, and the different speeds may be achieved in the latter case by one projectile making contact with the lever closer to its fulcrum than the other. The lever may be loaded by a spring or by a solenoid-operated device, for example. Such projectiles may be steel balls or other hard spheres, and there may be a receptacle to catch such projectiles as they fall away from the specimen after impact, and the guidance and/or safety tubes may be angled so that such projectiles falling into the receptacle avoid re-entering them.

The apparatus may include a safety device to arrest projectiles should they be launched when no specimen is in place.

In a preferred form of the apparatus there are three projectiles, which preferably make impact with the specimen at three different velocities in the ratio of about 1:2:4; this apparatus and the method of measuring the flow stress of a specimen by the use of it are particularly suitable in the case of the relatively small number of materials, and in particular of metals, which show appreciable work-hardening when subjected to strain at high temperature.

The invention will now be described, by way of example, with reference to the accompanying drawings in which.

Figure 1:
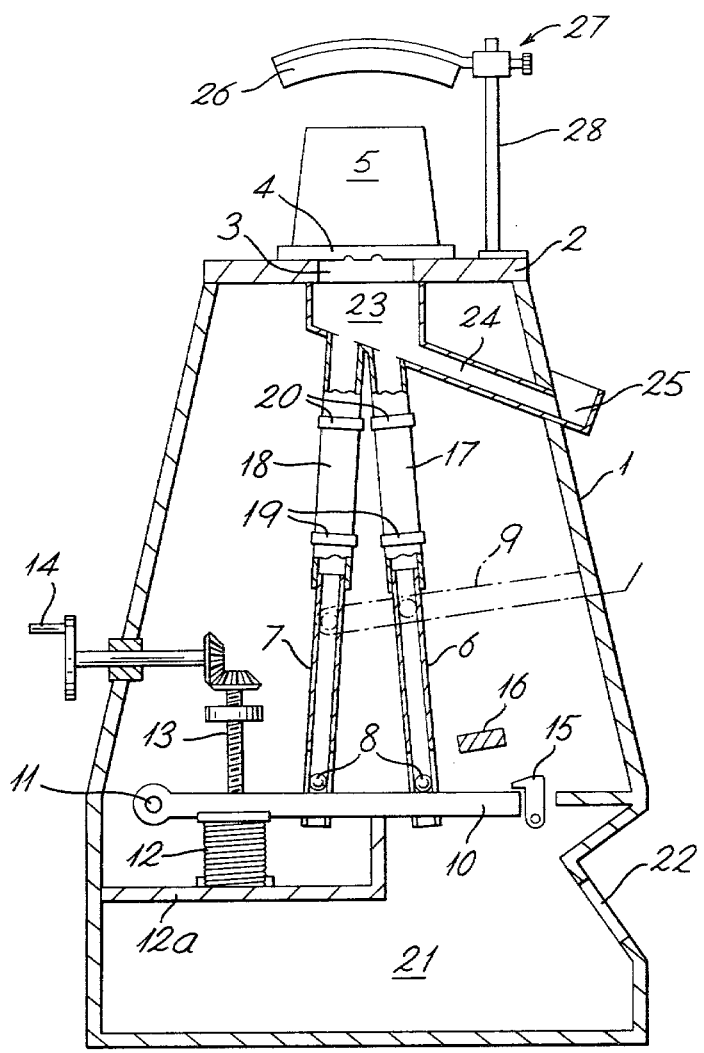
FIG. 1 is an elevation of one apparatus with a specimen in place ready for test.

In FIG. 1a framework 1 supports an insulated stage or table 2 having a central orifice 3. A plate-shaped specimen 4 is placed on table 2 over orifice 3 and is held down in place by a weight or clamp 5. Within frame 1 is located a firing mechanism comprising two tubes 6 and 7 acting as barrels. Projectiles in the form of identical steel balls 8 may be fed to barrels 6, 7 through a feed tube indicated diagrammatically at 9. Balls 8 are shown at rest against a lever 10, pivoted at a fulcrum 11 and loaded by a spring 12 which is supported by a bracket 12a and has been compressed by a screw 13 when turned by a handle 14. Lever 10 is held in the position shown, with spring 12 compressed, by a trigger 15. When the trigger is released, by external means not shown, lever 10 turns quickly until it meets stop 16, and propels balls 8 down barrels 6, 7 at different speeds, the ball in barrel 6 moving faster because its point of contact with lever 10 was further from fulcrum 11.

Barrels 6, 7 discharge into plastic shielding tubes 17, 18 of wider bore, and these tubes carry spaced detecting coils 19, 20 which are associated with electronic apparatus to determine and record the speed of each ball with reference to the time it takes to travel the distance between its respective coils 19, 20. The electronic apparatus is not shown, but may be accommodated within space 21 within frame 1; a window 22 may enable the operator to read the recorded velocities.

After emerging from tubes 17, 18 the balls strike the underside of specimen 4 at velocities substantially as determined by passage between their respective coils 19 and 20. Due to their different velocities they indent the underside differently, and after so doing fall away under gravity into a receptacle 23 and thence by a chute 24 to a collection point 25 from which they may be returned by hand to feeder 9. The alignment of tubes 17, 18 where they pass within receptacle 23 is so arranged that as the balls fall into the receptacle after striking the specimen they avoid the mouths of the tubes. Such captive balls or projectiles have been found to be very convenient from an operational point of view.

A thick foam plastic safety shield 26, clamped at 27 to a column 28 supported from table 2, arrests the balls should they be fired when no specimen is in place.

In one alternative version of the invention the projectiles could be in the form of cylinders with hemispherical ends that make impact with the specimen. The mass of such a projectile may be say ten times that of a single ball of the same spherical radius, and such a projectile thus has the advantage of producing an indentation of similar dimensions to that of a single ball, but at a lower velocity. This will reduce the average strain rate during the test and allow the measurement of flow stress at strain rates near to those used in hot working. Where such cylindrical projectiles are used it may be desirable to arrange the tubes 17 and 18 normal to the specimen surface in order to avoid slewing and subsequent loss of impact energy.

Figure 2:
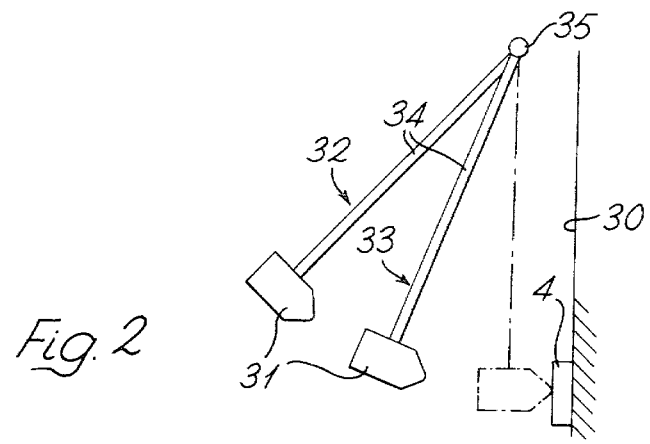
FIG. 2 is a diagrammatic elevation of part of another apparatus.

One method for calculating the high temperature flow stress ($\sigma$) or the strain rate ($\epsilon$) of a specimen by use of the apparatus of FIG. 1 or FIG. 2 will now briefly be described.

Experimental observations over a wide range of strain rates indicate that flow stress of many metals and other materials at constant temperature is related to strain rate by a power law of the kind $$\sigma = B \epsilon^m \quad (1)$$

where m and B are temperature-dependent constants. Assuming a hot metal specimen to be in a fully plastic state, then according to known indentation theory it may be deduced by consideration of energy changes that $$\frac{f(B,m)}{2-m} \cdot u^{(2-m)} = d^2 \quad (2)$$

$$\text{where } f(B,m) = \frac{0.56 W (2r)}{B} \quad (3)$$

where d is the total indentation depth achieved by a projectile of mass W and with a hemispherical end of radius r striking with an impact velocity u. If quantity d is known for the penetration of identical balls at two different velocities u, then (2-m) and hence m can be deduced from equation (3) above. This will allow determination of B since all other terms in the function f(B,m) are known. Experiments using the apparatus of FIG. 1, and calculations as above, have indicated that for specimens made from a range of alloys suitable indentations can be achieved with balls of 4 mm radius projected at velocities (u) between 20 and 120 m/s. Experiments in which the impact velocity of one ball has been about twice that of the other (say 30 and 60 m/s) have yielded particularly good results, and the temperature of specimens of various metals on test has varied between 300° and 1100° C. Under these conditions the average strain rates during the impacts are about $1300s^{-1}$. If cylindrical projectiles of a mass ten times that of a 4 mm ball are used, similar indentations can be achieved for impact velocities of 10 m/s and 20 m/s (i.e. strain rates near $300s^{-1}$).

It will be appreciated that heat will be gained by the specimen due to the dissipation of kinetic energy of the balls by means of plastic work, but heat will also be lost to the cold ball by conduction. The short contact time between ball and specimen, due to the downward-facing direction of the impact surface, is so small that cooling by the ball may be more than offset by the adiabatic heating which is implicit in high strain rate deformation.

In another alternative version of the invention shown in FIG. 2, specimen 4 is anchored to a stationary vertical surface 30 and the projectiles are the heads 31 of pendulums 32 and 33, the shafts 34 of which are of equal length and are pivoted about a common axis 35. The axis is located nearly vertically above specimen 4 so that the heads 31 are at the lowest point of their swing, and thus travelling horizontally, when they make impact with specimen 4. By releasing pendulums 32 and 33 simultaneously from starting positions at which they make different angles to the vertical, the two heads 31 will strike the specimen simultaneously, in a manner that eliminates the effect of the downward pull of gravity at the point of impact, and at different speeds that may possibly be ascertained with enough accuracy by reference only to well-known simple harmonic motion formulae and the dimensions of the apparatus, without the need for coils or other timing devices. In the example just described, of course, the effective mass of each projectile would be a function of the total mass of the head 31 (preferably heavy) and the shaft 34 (preferably light).

Figure 3:
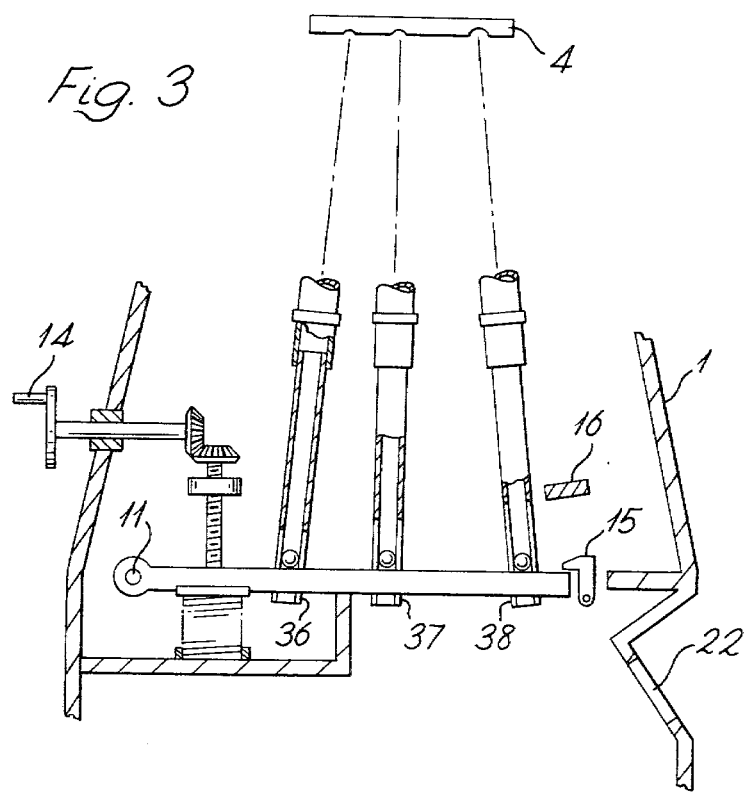
FIG. 3 is a diagrammatic elevation of part of yet another apparatus.

The apparatus of FIG. 3 is similar to that of FIG. 1 except that there are three steel balls 8 located in barrels 36, 37 and 38. These barrels are so located that the radii from fulcrum 11 of their points of intersection with the lever are in the ratio of about 1:2:4, with the result that the velocities at which the three balls strike the specimen 4 are in approximately the same ratio. Use of three projectiles and the parameters of the indentations produced by them enables flow stress to be calculated from the equation $$\sigma = A \cdot \epsilon^m \cdot \epsilon^n \ldots \quad (4)$$

which of course contains one more unknown than equation (1), and it has been found that the 1:2:4 ratio between the impact velocities of the three projectiles facilitates the accurate determination of A, n and m. While determination of flow stress by the relatively simple equation (1) has been found very satisfactory in the case of the great majority of metals whose flow stress is relatively independent of strain at high temperature, the more complicated equation (4) is better for the small number of metals that show appreciable work-hardening during strain at high temperature. For a material for which flow stress at high temperature is relatively independent of strain, of course the apparatus of FIG. 3 can still be used with one projectile omitted, and equation (1) applied.

Figure 4:
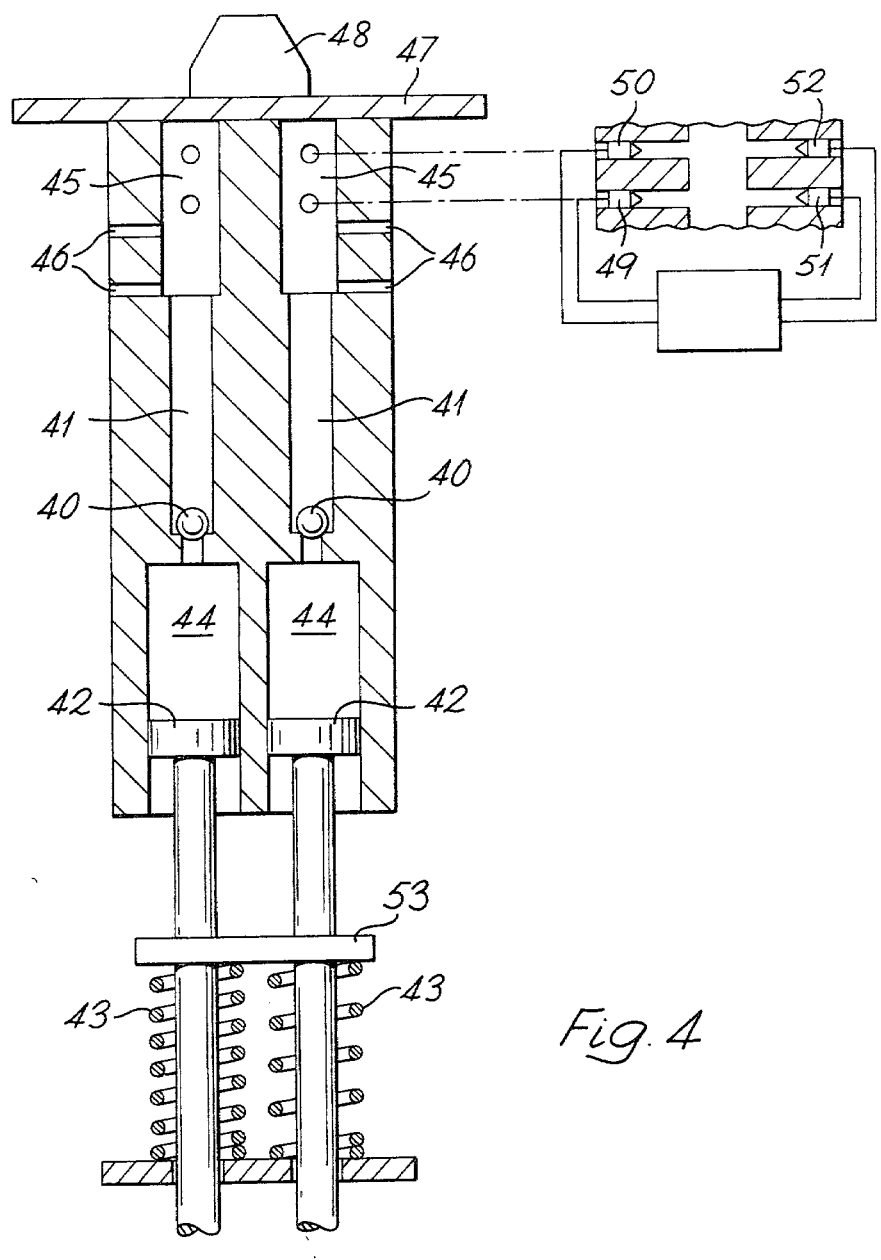
FIG. 4 is a schematic view of yet another apparatus.

In the apparatus of FIG. 4 two hard steel balls 40 are used as projectiles and are propelled by means of air pressure. The projectiles are loaded into two closely spaced barrels 41 and two pistons 42, powered by springs 43 of different stiffness and moving in cylinders 44, provide the necessary air pressure. After leaving barrels 41 the balls move into wide bore chambers 45 which are vented at 46 to release any excess pressure. The balls then move in free flight and make impact with the specimen 47 which is held by clamp 48. Just before impact the projectiles move through a device designed to measure their velocities. This device, shown separately from the main body of the apparatus in schematic FIG. 9, consists of two sensors for each barrel. References 49 and 50 denote infra-red sources and 51 and 52 are infra-red detectors and the separation of 51 and 52 (which is the same as that for 49 and 50) is accurately known. When the leading edge of a ball 40 passes the beam of radiation between 49 and 51 a signal is developed which starts an electronic timer. This timer is stopped when the leading edge passes the beam between 50 and 52. Times are recorded on digital meters to 1 μs and this allows the accurate calculation of the impact velocities.

Specimen 47 will typically be heated in a nearby furnace (not shown) and transferred to the clamp 48 which is asbestos-lined. A catch 53 releases the loaded pistons 43, and after striking the specimen 47 the balls 40 fall back under gravity into chambers 45 and barrels 41.

It will be appreciated that the methods of calculation given in this specification by way of example assume that the kinetic energy of a ball will be totally converted into plastic work. It is of course inevitable that some energy will be stored elastically and released as rebound energy. However the true elastic limit of metals at high temperatures is very low and since the flow stress tends to zero as the projectile velocity tends to zero also, the projectile-to-metal pressure will similarly tend to zero at the end of the indentation process. Under these circumstances, very little elastic energy will be released on rebound, even with the pendulum-type apparatus of FIG. 2.

It will also be appreciated that the invention is suitable for testing of specimens of a wide range of sizes and especially of shapes, provided a small flat exists or can be made to act as the target area where the indentations are to be made. The invention is also suitable for the testing of specimens at temperatures lower than ambient, as well as higher, and while particularly suitable for measuring the flow stress of specimens at high temperature it can also be used for measuring such characteristics, inter alia, as strength, and rate and extent of work hardening and recovery.

We claim:

1. Apparatus to measure strength characteristics of a specimen, comprising:
    means to support a specimen;
    means to launch at least two projectiles at different speeds towards said specimen, so that said projectiles strike said specimen at different striking speeds and so make different indentations upon it, and
    means to ascertain said striking speeds, whereby said characteristics may then be determined by calculations including said striking speeds and the dimensions of said indentations.

2. Apparatus according to claim 1 in which said means to ascertain said striking speeds comprise:
    optical sensors;
    means to generate beams illuminating said optical sensors and so disposed that said projectile intercepts said beams in succession in flight, and
    means to calculate said speed of said projectile from the time interval between interceptions.

3. Apparatus according to claim 1 in which said means to ascertain said striking speeds of a said projectile comprise:
    spaced coils located close to said specimen support means; electrical means to detect the successive passages of said projectile in proximity to each said coil of said pair, and means to calculate said speed from the time interval between said passages.

4. Apparatus according to claim 1 in which said projectiles are in the form of masses carried as pendulums.

5. Apparatus according to claim 4 in which said pendulums are so arranged that the centres of gravity of said masses are at the lowest points of their pendulum swings and are thus travelling horizontally when they strike said specimen.

6. Apparatus according to claim 4 including a common axis of support for said pendulums, and in which said pendulums are of equal length.

7. Apparatus according to claim 1 in which said launching means are arranged to launch said projectiles upwardly at the underside of a specimen held by said specimen support means.

8. Apparatus according to claim 7 in which said launching means are pneumatically operated.

9. Apparatus according to claim 8 in which said pneumatically-operated launching means comprise separate piston-and-cylinder devices for each of said at least two projectiles, and in which springs of different stiffness are used to drive the said pistons of said devices to achieve the said different striking speeds.

10. Apparatus according to claim 7 in which said launching means comprise a driven lever arranged so as to propel said projectiles by contact with them, the said different striking speeds being achieved by said projectiles making said contact with said lever at different distances from the fulcrum of said lever.

11. Apparatus according to claim 7 including protecting tubes in which said projectiles move for at least part of their free flight between their point of said launch and their striking said specimen.

12. Apparatus according to claim 1 including means to launch three projectiles so that they strike said specimen at three different striking speeds.

13. Apparatus according to claim 12 in which said means to launch said three projectiles are so arranged that said projectiles strike said specimen at striking speeds substantially in the ratio 1:2:4.

14. A method of measuring a strength characteristic of a specimen comprising, in succession:
    heating said specimen to a temperature different from ambient;
    launching at least two projectiles at said specimen so that they make impact with it substantially simultaneously but at different speeds, and
    determining said characteristic from a formula in which said different speeds of impact and the dimensions of the different indentations resulting from said impacts are relevant terms.

* * * * *